United States Patent
Guendel

(10) Patent No.: US 7,035,683 B2
(45) Date of Patent: Apr. 25, 2006

(54) METHOD FOR RESPIRATION-DEPENDENT TRIGGERING OF A MEDICAL IMAGE EXPOSURE

(75) Inventor: Lutz Guendel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 372 days.

(21) Appl. No.: 10/210,629

(22) Filed: Jul. 31, 2002

(65) Prior Publication Data

US 2003/0036708 A1 Feb. 20, 2003

(30) Foreign Application Priority Data

Jul. 31, 2001  (DE)  ................................ 101 37 170

(51) Int. Cl.
*A61B 5/05* (2006.01)
(52) U.S. Cl. ....................................... 600/421; 600/414
(58) Field of Classification Search ................ 600/421, 600/422, 423, 414, 407, 40–411; 324/306, 324/307, 308, 309
See application file for complete search history.

(56) References Cited

U.S. PATENT DOCUMENTS

| | | | |
|---|---|---|---|
| 3,524,058 A | 8/1970 | Robertson et al. | |
| 4,583,538 A | 4/1986 | Onik et al. | |
| 5,855,555 A * | 1/1999 | Crowely | 600/421 |
| 5,868,674 A * | 2/1999 | Glowinski et al. | 600/410 |
| 5,998,999 A * | 12/1999 | Richard et al. | 324/318 |
| 6,144,874 A | 11/2000 | Du | |
| 6,314,312 B1 | 11/2001 | Wessels et al. | |
| 6,408,202 B1 * | 6/2002 | Lima et al. | 600/423 |
| 6,430,429 B1 * | 8/2002 | Van Vaals | 600/410 |
| 6,529,766 B1 * | 3/2003 | Guendel | 606/427 |
| 6,560,475 B1 * | 5/2003 | Viswanathan | 600/410 |
| 6,587,706 B1 * | 7/2003 | Viswanathan | 600/410 |

FOREIGN PATENT DOCUMENTS

| | | |
|---|---|---|
| DE | OS 197 51 761 | 10/1998 |
| DE | OS 100 01 817 | 6/2001 |
| WO | WO 98/11822 | 3/1998 |

* cited by examiner

*Primary Examiner*—Daniel Robinson
(74) *Attorney, Agent, or Firm*—Schiff Hardin LLP

(57) ABSTRACT

In a method for respiration-dependent triggering of a data acquisition event in an imaging procedure, a navigation system is employed in order to reproduce the position of a body part moving due to respiration on a scale, particularly a linear scale. Triggering for the exposure of an image ensues at prescribed positions of a pointer relative to the scale, i.e. at prescribed scale values.

10 Claims, 1 Drawing Sheet

METHOD FOR RESPIRATION-DEPENDENT TRIGGERING OF A MEDICAL IMAGE EXPOSURE

BACKGROUND OF THE INVENTION

1. Field of the Invention

The present invention is directed to a method for triggering generation of an image of a subject dependent on respiration of the subject.

2. Description of the Prior Art

Many imaging methods in medicine such as, for example, computed tomography and magnetic resonance assume a non-moving subjects in the data acquisition measurement. Motion such as, for example, respiration leads to image artifacts. In an intervention with an imaging method wherein, for example, a needle must be guided to a small structure in the body, this leads to the fact that the target cannot be hit or cannot be reliably hit in the first attempt. This leads to a lengthening of the intervention and thus to a higher complication rate.

Attempts are therefore made in the biopsy of the lung to reliably hit the target during respiration pauses of the patient and under supervision with the imaging method. The image monitoring requires additional time and produces an additional radiation stress on the patient given employment of ionizing rays such as, for example in a computed tomography system. Given uncooperative patients, unconscious patients or children, this method cannot be employed, and full anesthesia with ventilation must be used, with associated risks.

Another alternative is to control of the respiration and/or the imaging method by means of a spirometer, but this is likewise rather complicated.

SUMMARY OF THE INVENTION

An object of the present invention is to provide a method for respiration dependent triggering of a data acquisition event in an imaging procedure that enables artifact-free, reproducible images as well as unproblematical interventions regardless of the cooperation of the patient.

For achieving this object a navigation system is inventively employed in order to reproduce the position of a body part moving due to respiration on a scale. particularly a linear scale, and a triggering for the exposure (data gathering event) of an image ensues at prescribed positions on the scale, i.e. at prescribed scale values.

In a very simple way, the inventive method assures that an image exposure, particularly repeated image exposures as well, always occur in the same motion stage (phase). The start of the scale can, for example, represent the exhaled condition, the end of the scale can represent the inhaled condition and a pointer can represent the momentary respiration position. By observing the migrating pointer along the scale an operator can trigger an exposure at any arbitrarily, prescribed point in time, i.e. in the exhaled or in the inhaled condition or in an intermediate stage. Of course, such triggering can ensue automatically at a prescribed point on the scale with electronic or computerized monitoring of the migrating pointer. In order to produce the scale, a marker can be secured to the body of the patient in the simplest case, the respective position of the marker being displayed on the scale.

The inventive respiration-triggering method is particularly suited for interventions at a moving body, for example for biopsies or the like. To this end, the intervention is implemented after the production of a respiration-triggered image, possibly in steps, at the same time in a subsequent motion cycle of which the production of the image occurred in a previous cycle, while targeting the fixed target point of the still image.

In the simplest case, the angle and, possibly, the distance from the known starting position of the intervention instrument, particularly a biopsy needle, are initially measured in the image. The appropriate displacement of the intervention instrument subsequently ensues at the same triggering time (in a subsequent cycle) at which the image was produced.

In an embodiment of the invention the tip of the intervention instrument is continuously identified via a position acquisition system and is mixed into the stationary, triggered image, and a displacement of the intervention instrument in the still image with the mixed-in instrument position ensues at the triggering time, i.e. at the same scale position at which the image was registered.

DESCRIPTION OF THE PREFERRED EMBODIMENTS

Figure 1:
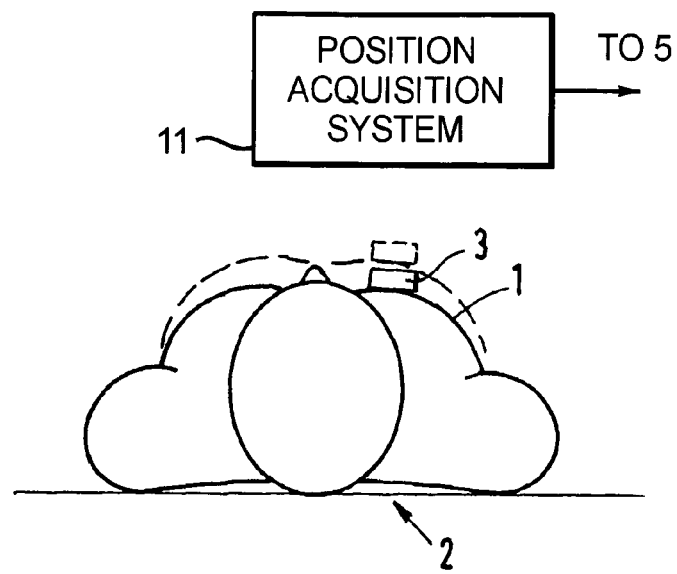
FIG. 1 is a schematic illustration of a prone patient registered as seem from the head, with a marker secured to the chest for implanting the inventive method.
Figure 2:
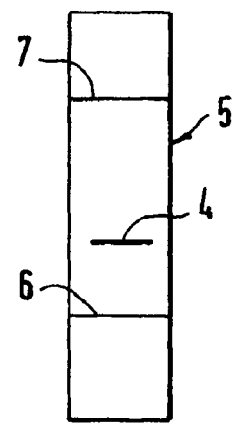
FIG. 2 is an illustration of a scale having a pointer reproducing the position of the marker that moves between two limit values for the inhaled and the exhaled condition.

A marker 3 is secured on the chest 1 of the patient 2 shown in FIG. 1, the position of the marker 3 being acquired with a position acquisition system 14 and being indicated or seen as movement of a pointer 4 along a scale 5. The pointer 4 moves between the limit positions 6 and 7 that correspond respectively to the exhaled and the inhaled conditions. A triggering of the imaging system ensues either manually or automatically at an arbitrary point in time, at the exhaled criterion, at the inhaled condition or at a prescribed intermediate time, so that a series of comparable exposures can be produced respectively at the same motion stage in each of a number of motion cycles.

Figure 3:
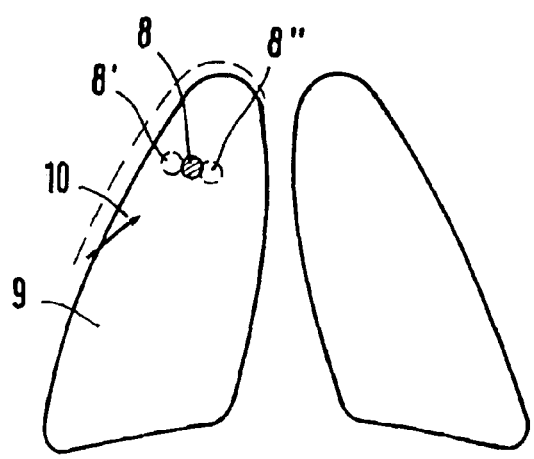
FIG. 3 is a schematic illustration of a lung with a tumor that is displaced during respiration and that is to be punctured by a biopsy needle.

The inventive triggering method is particularly suited for an intervention, for example a biopsy of a tumor 8 on a lobe 9 of the lung, whereby this tumor 8 moves between the broken-line positions 8' and 8" during respiration. In order nonetheless to be able to implement a simple intervention, i.e. a simple biopsy, an exposure wherein the tumor 8 is in the solid-line position in FIG. 3 is first made at a specific, prescribed respiration condition—the inhaled or the exhaled position is preferred but an intermediate position also can be selected given a difficult position that is hard to recognize. The tip 10 of the intervention instrument, i.e., for example, of the biopsy needle, is continuously identified via a position acquisition system and this position is mixed into the stationary, triggered image according to FIG. 3. At the same triggering time (in a subsequent cycle) at which the image was made, i.e. at the same position of the pointer 4 on the scale 5, the instrument is displaced to the tumor 8 in the image, since it is known that the tumor is located exactly in this position at this trigger time even though no image observation at all is ensuing at the current moment. In the case of complicated interventions or biopsies, the displace- Although modifications and changes may be suggested by those skilled in the art, it is the intention of the inventor to embody within the patent warranted hereon all changes and modifications as reasonably and properly come within the scope of his contribution to the art.

What is claimed is:

1. A method for respiration-dependent triggering of production of a medical image, comprising the steps of:
    designating a position relative to a scale of a body part of a subject, said body part moving due to respiration of the subject by securing a marker, separate from said scale, to said body part and indicating a position of said marker on said scale; and
    triggering at least one data acquisition event for obtaining an image of said subject when said designation of said body part is at a prescribed position relative to said scale.

2. A method as claimed in claim 1 comprising employing a linear scale as said scale.

3. A method as claimed in claim 1 comprising employing a scale having a plurality of scale values, and wherein the step of triggering said at least one data acquisition event comprises triggering said at least one data acquisition event when said designation of said movement of said body part is at a predetermined scale value.

4. A method for respiration-dependent trigging of production of a medical image, comprising:
    designating a position relative to a scale of a body part of a subject, said body part moving due to respiration of the subject;
    triggering at least one data acquisition event for obtaining an image of said subject when said designation of said body part is at a prescribed position relative to said scale;
    introducing an intervention instrument into said subject toward a target point at a fixed location in said image; and
    triggering said introduction of said intervention instrument, in a subsequent motion cycle of said subject, when said designation of said body part in said subsequent cycle is at said prescribed position relative to said scale.

5. A method as claimed in claim 4 comprising introducing said intervention instrument into said subject in a plurality of successive steps, and initiating each of said plurality of successive steps, in respective subsequent motion cycles of said subject, when said designation of the position of said body part is at said prescribed position relative to said scale.

6. A method as claimed in claim 4 wherein said intervention instrument has a tip, and identifying an angle of said tip in said image relative to said starting position.

7. A method as claimed in claim 6 comprising additionally determining a distance of said tip from said known starting position.

8. A method as claimed in claim 6 comprising continuously monitoring and identifying a position of said tip of said intervention instrument using a position acquisition system and mixing a designation of said tip into said image and, in respective subsequent motion cycles of said subject, briefly displacing said intervention instrument into said subject when said designation of said body part is at said prescribed position relative to said scale.

9. A method as claimed in claim 1 wherein the step of indicating a position of said marker on said scale comprises detecting, with a position acquisition system, a physical position of said marker on said body part, and indicating said position of said marker on said scale dependent on the detected physical position of the marker on the body part.

10. A method as claimed in claim 9 comprising indicating said position relative to said scale by a moving pointer in said scale, said pointer moving in said scale dependent on said physical position of said marker secured to said body part detected by said position acquisition system.

* * * * *